(12) United States Patent
Weiß et al.

(10) Patent No.: US 10,933,215 B2
(45) Date of Patent: Mar. 2, 2021

(54) HOSE LINE AND METHOD FOR PRODUCING SAME

(71) Applicant: B. BRAUN MELSUNGEN AG, Melsungen (DE)

(72) Inventors: André Weiß, Guxhagen (DE); Oliver Kahlen, Gudensberg (DE)

(73) Assignee: B. BRAUN MELSUNGEN AG, Melsungen (DE)

( * ) Notice: Subject to any disclaimer, the term of this patent is extended or adjusted under 35 U.S.C. 154(b) by 185 days.

(21) Appl. No.: 15/949,492

(22) Filed: Apr. 10, 2018

(65) Prior Publication Data

US 2018/0289923 A1 Oct. 11, 2018

(30) Foreign Application Priority Data

Apr. 11, 2017 (DE) .......................... 102017206154.5

(51) Int. Cl.
*A61M 25/00* (2006.01)
*B23K 26/24* (2014.01)
*B23K 26/38* (2014.01)

(52) U.S. Cl.
CPC ...... *A61M 25/0013* (2013.01); *A61M 25/007* (2013.01); *A61M 25/0015* (2013.01);
(Continued)

(58) Field of Classification Search
CPC .............. A61M 25/003; A61M 25/007; A61M 2025/0031; A61M 2025/0037; F16L 11/20; F16L 11/22
See application file for complete search history.

(56) References Cited

U.S. PATENT DOCUMENTS

| 4,454,887 A | 6/1984 | Kruger |
| 4,995,863 A | 2/1991 | Nichols et al. |

(Continued)

FOREIGN PATENT DOCUMENTS

| DE | 3310870 A1 | 10/1983 |
| DE | 4037641 A1 | 6/1992 |

(Continued)

OTHER PUBLICATIONS

Extended European Search Report for European Application No. 18 165 761.0, dated Sep. 13, 2018, with partial English translation, 6 pages.

(Continued)

*Primary Examiner* — Laura A Bouchelle
*Assistant Examiner* — Anh Bui

(57) ABSTRACT

A hose line includes a sheath extending axially between a first hose end and a second hose end, and has an outer face and an inner face, an axial passage enclosed by the inner face and extending between the hose ends, a radial passage which extends through the sheath and connects the axial passage to the outer face, and a closure which is arranged between the radial passage and the second hose end and closes the axial passage in a fluid-tight manner. The radial passage is formed by a sheath portion which is bent and partially separated from the rest of the sheath along a partition line. The closure is formed by placing the sheath portion onto the inner face and connecting the sheath portion to the inner face in a fluid-tight manner. The hose line can be used in a catheter hose line.

7 Claims, 3 Drawing Sheets

(52) U.S. Cl.
CPC ......... *A61M 25/0029* (2013.01); *B23K 26/24* (2013.01); *B23K 26/38* (2013.01); *A61M 2025/0031* (2013.01); *A61M 2025/0034* (2013.01)

(56) References Cited

U.S. PATENT DOCUMENTS

| | | | |
|---|---|---|---|
| 5,374,245 A * | 12/1994 | Mahurkar | A61M 25/001 604/43 |
| 5,464,398 A | 11/1995 | Haindl | |
| 9,168,355 B2 | 10/2015 | Braga | |
| 2005/0085761 A1 | 4/2005 | Wang et al. | |
| 2008/0249501 A1 | 10/2008 | Yamasaki | |
| 2010/0081986 A1 * | 4/2010 | Matson | A61M 25/0075 604/6.16 |
| 2010/0145187 A1 * | 6/2010 | Weber | A61B 8/0833 600/424 |

FOREIGN PATENT DOCUMENTS

| | | |
|---|---|---|
| EP | 0263645 A2 | 4/1988 |
| EP | 1905476 A2 | 4/2008 |
| WO | 2008052764 A2 | 5/2008 |

OTHER PUBLICATIONS

German Search Report for German Application No. 10 2017 206 154.5, dated Jan. 2, 2018 with partial translation, 10 pages.

* cited by examiner

HOSE LINE AND METHOD FOR PRODUCING SAME

RELATED APPLICATION(S)

This application is related to and claims the benefit of priority of German patent application DE 10 2017 206 154.5, filed Apr. 11, 2017, the content of which is hereby incorporated by reference into this application.

FIELD

The present disclosure relates generally to hose lines, and more particularly to a hose line with a radial passage.

BACKGROUND

A hose line of this kind is generally known in the field of fluid technology and can be used for the radial discharge of a fluid. For this purpose, the known hose line has a radial passage, which branches off laterally from an axial passage, and a closure. The closure is arranged in the axial passage axially behind the radial passage and closes the axial passage in a fluid-tight manner. The radial passage is introduced into the hose sheath of the hose line by drilling or punching. The closure is arranged in the form of a separate structural element or a filling material in the axial passage.

SUMMARY

The object of the present disclosure is to make available a hose line of the aforementioned type which can be produced in a particularly advantageous manner and which ensures functionally appropriate sealing.

Such a hose line can feature:

a hose sheath which extends axially between a first hose end and a second hose end and has a sheath outer face and a sheath inner face, at least one axial passage enclosed by the sheath inner face and extending axially between the hose ends, at least one radial passage which extends substantially radially through the hose sheath and fluidically connects the at least one axial passage to the sheath outer face, and at least one closure which is arranged between the radial passage and the second hose end and closes the at least one axial passage in a fluid-tight manner in the direction of the second hose end.

The object of the present disclosure is achieved by the fact that the at least one radial passage is formed by a hose sheath portion which is bent substantially radially inwards and which is partially separated from the rest of the hose sheath along a partition line, wherein the at least one closure is formed by means of the hose sheath portion being placed onto the sheath inner face and being connected thereto in a fluid-tight manner. By virtue of the solution according to the disclosure, it is possible to do without an additional structural element for closing the axial passage. Instead, the closure is formed, according to the disclosure, by means of the hose sheath portion being partially separated from the rest of the hose sheath along the partition line, being bent inwards, placed onto the sheath inner face and connected thereto in a fluid-tight manner. The radial passage is in this case formed as it were by the partial separation from the rest of the hose sheath and by the inwardly directed bending of the hose sheath portion. Accordingly, it is possible to dispense with separate introduction of the radial passage, for example by means of punching or the like, and material can thereby be saved. Within the context of this disclosure, partial separation is to be understood as meaning that the hose sheath portion is at any rate connected integrally to the rest of the hose sheath along an edge region. Within the context of this disclosure, a radial passage is to be understood as an opening through which a fluid can flow out of the hose line and/or can flow into the hose line, thereby permitting a stream of fluid from the axial passage to the radial passage and/or vice versa.

The solution according to the disclosure is particularly advantageously suitable for catheter hoses, in particular for multi-lumen central venous catheters. However, the solution according to the disclosure can also be used in the field of general fluid technology, where lateral outlet openings on hose lines are important.

In one embodiment, the partition line has a tongue-shaped profile in a viewing direction directed radially onto the radial passage. The profile of the partition line to this extent comprises a first axially extending line portion, a substantially semi-circular line portion, and a third line portion which extends substantially antiparallel to and at a distance from the first line portion. This tongue-shaped profile of the partition line permits particularly tight contact and an advantageous connection of the hose portion to the sheath inner face.

In a further embodiment, the hose line is a medical catheter hose, in particular a central venous catheter, the first hose end is a proximal catheter hose end, the second hose end is a distal catheter hose end, the axial passage is a first lumen, and the radial passage is a catheter side channel. In this way, a catheter hose is formed that can be produced in a particularly advantageous manner and that is sealed in what is a functionally appropriate manner.

In a further embodiment, at least one second lumen is provided which is separated from the first lumen in a fluid-tight manner by an axially extending partition wall, wherein the hose sheath portion is connected in a fluid-tight manner to the partition wall. In conventional multi-lumen catheters, the closure between the catheter side channel and the distal catheter hose end is formed by means of shaped cord or paste-like moulding compounds. This is complex and, due to the technology used, may result in incomplete sealing. It may in some cases lead to the accumulation and proliferation of microorganisms in the region of the closure. Consequently, infections cannot be ruled out. This embodiment overcomes these disadvantages and provides a particularly advantageous multi-lumen catheter.

The disclosure further relates to a method for producing a hose line according to the above embodiments.

The method according to the disclosure comprises the following steps: the hose sheath is opened up along the partition line; the hose sheath portion thus obtained is bent inwards in the radial direction, and the hose sheath portion is placed onto the sheath inner face; the hose sheath portion is connected in a fluid-tight manner to the sheath inner face. By virtue of the method according to the disclosure, the closure can be created without additional structural elements or without filling the axial passage with moulding compound. Particularly cost-effective production is thus achieved.

In a further embodiment, the opening-up is effected by means of laser cutting. By virtue of this embodiment of the method according to the disclosure, the geometry of the radial passage can be produced with a particularly high degree of dimensional accuracy and high quality.

In a further embodiment, the fluid-tight connection is effected by means of laser welding. Particularly reliable sealing can be obtained in this way. If the hose sheath is also opened up by means of laser, particularly cost-effective production can be achieved, since one and the same technology is used for producing the radial opening and for producing the closure.

BRIEF DESCRIPTION OF THE DRAWING FIGURES

Further advantages and features will become clear from the following description of illustrative embodiments that are shown in the drawings.

DETAILED DESCRIPTION

Figure 1:
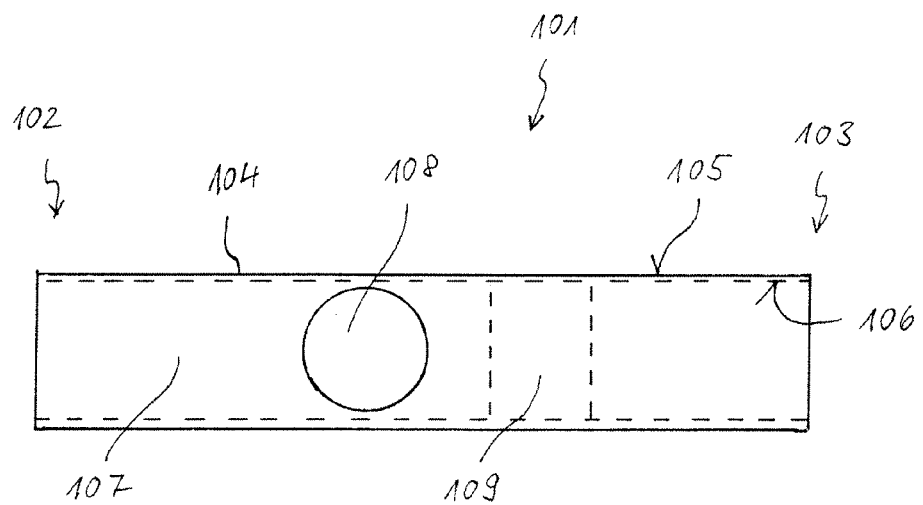
FIG. 1 shows a schematic plan view of a generic hose line according to the prior art.
Figure 2:
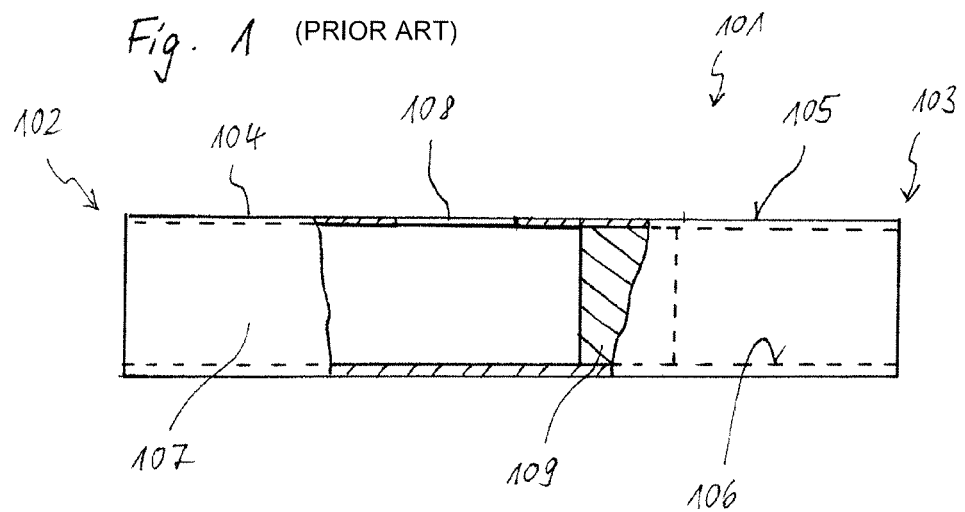
FIG. 2 shows a partially sectioned side view of the generic hose line according to FIG. 1.

A generic hose line 101 according to FIGS. 1 and 2 is provided in the field of fluid technology. The generic hose line 101 has a hose sheath 104 which extends axially between a first hose end 102 and a second hose end 103 and which has a sheath outer face 105 and a sheath inner face 106. The generic hose line 101 additionally has an axial passage 107 and a radial passage 108. The axial passage 107 is enclosed by the sheath inner face 106 and extends in the axial direction between the first hose end 102 and the second hose end 103. The radial passage 108 extends, in the shape of a circular cylindrical recess, in the radial direction through the hose sheath 104 and in this way forms a fluid-conveying connection from the axial passage 107 to the sheath outer face 105 of the hose line 101. Moreover, the generic hose line 101 has a closure 109. The closure 109 is arranged in the axial direction between the radial passage 108 and the second hose end 103 and in this way closes the axial passage 107 on one side in the direction of the second hose end 103. In the generic hose line 101, the closure 109 is formed by a separate structural element connected in a fluid-tight manner to the sheath inner face 106. Alternatively, the closure 109 can be formed by a plastic filling compound or the like. In the known hose line 101, the radial passage 108 is produced by complete removal of a hose sheath portion from the hose sheath 104 by means of punching, cutting or the like.

A first embodiment of a hose line 1 according to the disclosure (cf. FIGS. 3 and 4) is provided in the field of fluid technology for the radial discharge of a fluid. The hose line 1 according to the disclosure has a hose sheath 4 which extends axially between a first hose end 2 and a second hose end 3 and which has a sheath outer face 5 and a sheath inner face 6. An axial passage 7, arranged inside the hose sheath 4 and enclosed by the sheath inner face 6, extends between the hose ends 2 and 3. Branching off from the axial passage 7, a radial passage 8 extends substantially in the radial direction through the hose sheath 4, such that a fluid-conveying connection is created between the axial passage 7 and the sheath outer face 5. The radial passage 8 is formed by the bending-in of a hose sheath portion 11 that is partially separated from the rest of the hose sheath 4 along a partition line 10. The hose sheath portion 11 is detached from the rest of the hose sheath 4 along the partition line, in a manner to be described in more detail, and is connected integrally to the hose sheath 4 in a front end region 12. As will be seen from the partially sectioned side view in FIG. 4, the hose sheath portion 11, starting from the front end region 12, extends radially downwards in an oblique direction as far as a wall portion 13 of the sheath inner face 6 opposite the radial passage 8 and bears on said sheath inner face 6. Moreover, the hose sheath portion 11 is connected in a fluid-tight manner to the wall portion 13 of the sheath inner face 6, in a manner to be described in more detail. A closure 9 is thus formed between the radial passage 8 and the second hose end 3 and closes the axial passage 7 on one side in the direction of the second hose end 3.

Figure 3:
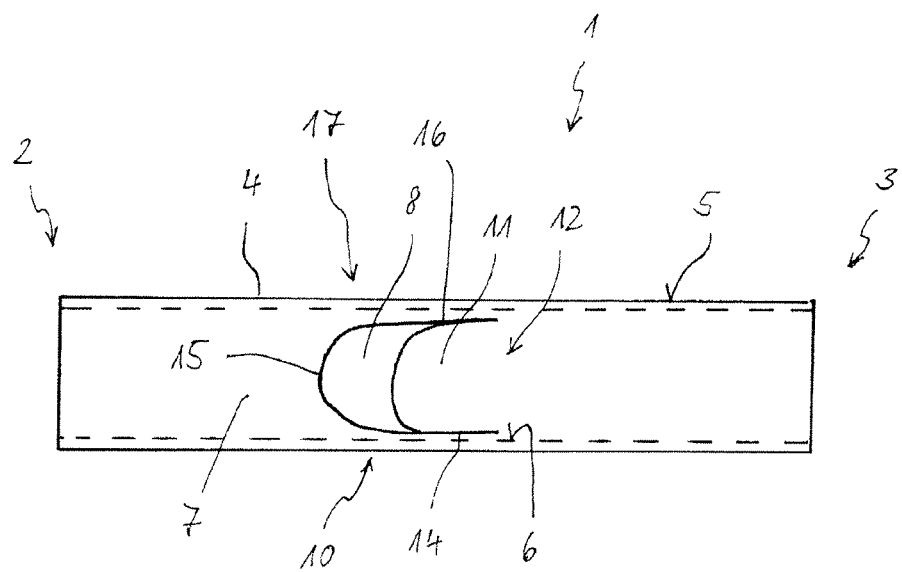
FIG. 3 shows a schematic plan view of a first embodiment of a hose line.
Figure 4:
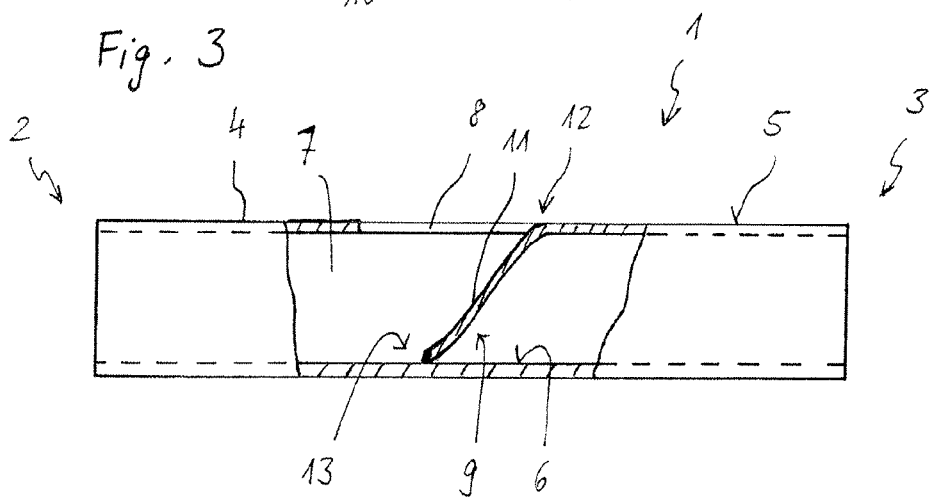
FIG. 4 shows a partially sectioned side view of the hose line according to FIG. 3.

As will be seen from FIG. 3, the partition line 10 has a first axially extending line portion 14, a substantially semi-circular second line portion 15, and a third line portion 16 which extends substantially antiparallel to and at a distance from the first line portion 14. This results in a tongue-shaped profile 17 of the partition line 10.

Figure 5:
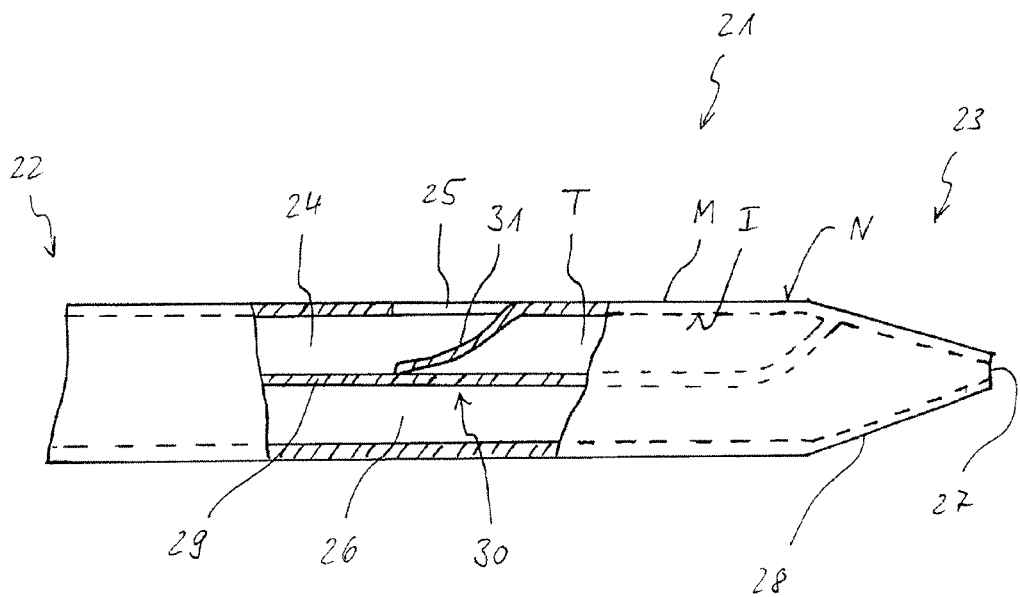
FIG. 5 shows a partially sectioned side view of a second embodiment of a hose line which is provided in the field of medical technology.

A second embodiment, as shown in FIG. 5, is provided for use in the field of medical technology, in particular for use in infusion therapy. This embodiment has, as hose line, a medical catheter hose 21, wherein the first hose end is a proximal catheter hose end 22, the second hose end is a distal catheter hose end 23, the axial passage is a first lumen 24, and the radial passage is a catheter side channel 25. The catheter hose 21 additionally has a second lumen 26 which extends between the proximal catheter hose end 22 and the distal catheter hose end 23 and which merges into an outlet opening 27 of a catheter tip 28. The first lumen 24 and the second lumen 26 are separated from each other in a fluid-tight manner by a substantially axially extending partition wall 29. To close off a dead volume T between the catheter tip 28 and the catheter side channel 25 in a fluid-tight manner, a closure 30 is provided in the form of a substantially radially inwardly bent hose sheath portion 31 of the catheter hose 21. The hose sheath portion 31 is separated partially from the sheath M of the catheter hose 21 along a partition line (not shown in any detail) that extends on the sheath outer face N analogously to the partition line 10 of the first illustrative embodiment according to FIGS. 3 and 4. To permit fluid-tight closure of the dead volume T, the hose sheath portion 31 is connected in a fluid-tight manner to the partition wall 29 and the adjoining sheath inner face I of the catheter hose 21, more precisely of the first lumen 24.

Figure 6:
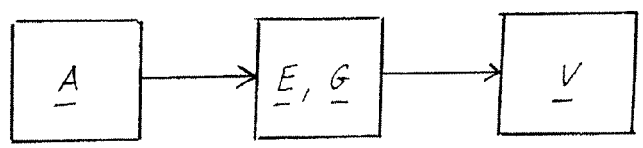
FIG. 6 shows a schematic representation of a method for producing a hose line in accordance with one embodiment.

As will be seen from FIG. 6, in the method according to the disclosure for producing a hose line according to the preceding embodiments, the hose sheath 4, 21 is first of all opened up (A) along a partition line, the hose sheath portion 11, 31 thus obtained is bent inwards (E) in the radial direction and placed (G) onto the sheath inner face and then connected (V) to the latter in a fluid-tight manner. In an embodiment of the method according to the disclosure not detailed here, the hose sheath is opened up A by means of laser cutting, and the fluid-tight connection V is obtained by means of laser welding.

The invention claimed is:

1. A hose line comprising:
   a hose sheath which extends axially between a first hose end and a second hose end, the hose sheath having a sheath outer face and a sheath inner face;
   at least one axial passage enclosed by the sheath inner face and extending axially between the hose ends;

at least one radial passage which extends substantially radially through the hose sheath and fluidically connects the at least one axial passage to the sheath outer face; and at least one closure which is arranged between the radial passage and the second hose end and closes the at least one axial passage in a fluid-tight manner in the direction of the second hose end, wherein the at least one radial passage comprises a portion of the sheath outer face, the portion of the sheath outer face extending continuously from an adjacent portion of the sheath outer face and substantially radially inwards into the axial passage to form a portion of the axial passage, with a fluid-tight connection located between the portion of the sheath outer face and the sheath inner face, and wherein the at least one axial passage forms a hollow dead volume that is closed off between the portion of the sheath outer face and the second hose end.

2. The hose line according to claim 1, wherein the portion of the sheath outer face is partially defined by a partition line, wherein the partition line has a tongue-shaped profile in a viewing direction directed radially onto the radial passage.

3. The hose line according to claim 1, wherein the hose line comprises a medical catheter hose, the first hose end comprises a proximal catheter hose end, the second hose end comprises a distal catheter hose end, the axial passage comprises a first lumen, and the radial passage comprises a catheter side channel.

4. The hose line according to claim 3, wherein at least one second lumen is provided which is separated from the first lumen in a fluid-tight manner by an axially extending partition wall, wherein the hose sheath portion is connected in a fluid-tight manner to the partition wall.

5. A method for producing a hose line comprising the steps of:
providing a hose line comprising:

a hose sheath which extends axially between a first hose end and a second hose end, the hose sheath having a sheath outer face and a sheath inner face, wherein the sheath outer face comprises at least one partition line;

at least one axial passage enclosed by the sheath inner face and extending axially between the hose ends;

opening up the hose sheath along the at least one partition line to form at least one hose sheath portion;

bending the at least one hose sheath portion thus obtained inwardly in the radial direction to form at least one radial passage that extends substantially radially through the hose sheath and fluidically connects the at least one axial passage to the sheath outer face, and placing the at least one hose sheath portion onto the sheath inner face; and connecting the at least one hose sheath portion in a fluid-tight manner to the sheath inner face, thereby forming at least one closure arranged between the radial passage and the second hose end to close the at least one axial passage in a fluid-tight manner in the direction of the second hose end, wherein the at least one radial passage comprises a portion of the sheath outer face, the portion of the sheath outer face extending continuously from an adjacent portion of the sheath outer face and substantially radially inwards into the at least one axial passage to form a portion of the axial passage, with a fluid-tight connection located between the portion of the sheath outer face and the sheath inner face.

6. The method according to claim 5, wherein the step of opening up the hose sheath comprises laser cutting.

7. The method according to claim 5, wherein the step of connecting the hose sheath portion in a fluid-tight manner comprises laser welding.

* * * * *